(12) United States Patent
Nguyen (10) Patent No.: US 10,960,230 B2
(45) Date of Patent: Mar. 30, 2021

(54) CALIBRATION OF HYPOXIC REGION FOCUSED RADIOTHERAPY TREATMENT PLANS

(71) Applicant: Nam P. Nguyen, Washington, DC (US)

(72) Inventor: Nam P. Nguyen, Washington, DC (US)

( * ) Notice: Subject to any disclaimer, the term of this patent is extended or adjusted under 35 U.S.C. 154(b) by 96 days.

(21) Appl. No.: 16/210,590

(22) Filed: Dec. 5, 2018

(65) Prior Publication Data

US 2019/0105516 A1 Apr. 11, 2019

Related U.S. Application Data (63) Continuation-in-part of application No. 14/745,188, filed on Jun. 19, 2015, now Pat. No. 10,166,405, which is a continuation-in-part of application No. 14/436,394, filed as application No. PCT/US2013/065283 on Oct. 16, 2013, now Pat. No. 9,895,554, which is a continuation-in-part of application No. 13/652,821, filed on Oct. 16, 2012, now abandoned.

(51) Int. Cl.
*A61N 5/10* (2006.01)
*A61B 6/03* (2006.01)
*G01T 1/29* (2006.01)
*A61B 6/00* (2006.01)
*A61B 6/12* (2006.01)

(52) U.S. Cl.
CPC ............ *A61N 5/1075* (2013.01); *A61B 6/037* (2013.01); *A61B 6/5217* (2013.01); *A61N 5/1031* (2013.01); *A61N 5/1039* (2013.01); *A61N 5/1064* (2013.01); *A61N 5/1077* (2013.01); *G01T 1/2985* (2013.01); *A61B 6/12* (2013.01); *A61B 6/469* (2013.01); *A61N 2005/1076* (2013.01)

(58) Field of Classification Search
CPC .. A61N 5/1031; A61N 5/1037; A61N 5/1039; A61N 5/1042; A61N 5/1045; A61N 5/1047; A61N 5/1069; A61N 5/107; A61N 5/1071; A61N 5/1075; A61N 2005/1076
See application file for complete search history.

(56) References Cited

U.S. PATENT DOCUMENTS

| 7,606,405 B2 | 10/2009 | Sawyer et al. |
| 8,173,983 B1 | 5/2012 | Sahadevan |

(Continued)

FOREIGN PATENT DOCUMENTS

WO  WO2014062830 A1  4/2014

OTHER PUBLICATIONS

Sause, WT et al.; Fraction size in external beam radiation therapy in the treatment of melanoma; Int J Radiat Oncol Biol Phys; Mar. 1991; 20(3):429-32 (Abstract).

(Continued)

*Primary Examiner* — Carrie R Dorna
(74) *Attorney, Agent, or Firm* — Nguyen Tarbet LLC (57) ABSTRACT

The present invention features calibration methods for radiotherapy treatment plans. An image-guided radiotherapy system for tumor treatment featuring a hypoxic-region-focused (HRF) radiation dose is calibrated using a phantom. The treatment plans may also feature a boosted dose to the resistance region of the tumor. The HRF radiation dose may be greater than 120% of a predetermined prescribed radiation dose for the tumor.

6 Claims, 5 Drawing Sheets

(56) References Cited

U.S. PATENT DOCUMENTS

| | | |
|---|---|---|
| 8,238,520 B2 | 8/2012 | Nord et al. |
| 9,895,554 B2 | 2/2018 | Nguyen |
| 2005/0041843 A1 | 2/2005 | Sawyer |
| 2006/0067469 A1 | 3/2006 | Dooley et al. |
| 2007/0014454 A1 | 1/2007 | Sawyer et al. |
| 2008/0267351 A1* | 10/2008 | Spies .................. A61N 5/1039 378/65 |
| 2009/0130098 A1 | 5/2009 | Goodman et al. |
| 2010/0228116 A1 | 9/2010 | Lu et al. |
| 2010/0322381 A1 | 12/2010 | Stahl et al. |
| 2011/0075806 A1 | 3/2011 | Nord et al. |
| 2012/0326057 A1 | 12/2012 | Remeijer et al. |
| 2014/0252227 A1 | 9/2014 | Sasai |
| 2015/0246246 A1 | 9/2015 | Nguyen |
| 2016/0051841 A1 | 2/2016 | Nguyen |
| 2018/0200537 A1* | 7/2018 | Gustafsson .......... A61N 5/1075 |

OTHER PUBLICATIONS

Radiation Therapy Oncology Group, RTOG 0920, A Phase III Study of Postoperative Radiation Therapy (IMRT) +/− Cetuximab for Locally Advanced Resected Head and Neck Cancer, Dec. 6, 2010.

Nancy Lee, M.D, Adam Garden, M.D., Alan Kramer, M.D, Ping Xia, Ph.D., Radiation Therapy Oncology Group, RTOG 0225: A Phase II Study of Intensity Modulated Radiation Therapy (IMRT) +/− Chemotherapy for Nasopharyngeal Cancer, May 26, 2005.

Schofield, Debbie et al., Review and guidelines for treating head and neck tumors using IMRT and VMAT, AAPM 2010.

Schofield, Debbie; Farber, Dana, "The Use of IMRT in the Treatment of Head and Neck Cancer"; 2012.

Mayo, Charles; "Review and guidelines for treating head and neck tumors using IMRT and VMAT"; 2012.

Wu et al. "Simultaneous Integrated Boost Intensity-Modulated Radiotherapy for Locally Advanced Head-and-Neck Squamous Cell Carcinomas. I: Dosimetric Results." International Journal of Radiation Oncology Biology Physics. vol. 56, No. 2, 2003, pp. 573-585.

Teh et al. "The treatment of primary and metastatic renal cell carcinoma (RCC) with image-guided stereotactic body radiation therapy (SBRT)." Biomedical Imaging and Intervention Journal. vol. 3, No. 1, 2007.

Verwer et al. Positron emission tomography to assess hypoxia and perfusion in lung cancer. World J Clin Oncol Dec. 10, 2014; 5(5): 824-844.

Fleming et al. Imaging tumour hypoxia with positron emission tomography. British Journal of Cancer (2015) 112, 238-250.

European Search Report Issued for EP Application No. 19158135.4 dated Jul. 25, 2019.

* cited by examiner

| Hotspots |
|---|
| • 105%+ |
| • DFCI: Aim for 5%, <110% |
| • UMass: aim for <110%. Typically 8% vol <10% (will accept ~10% of PTV > 110% if necessary) |
| • 105-110% (MDACC) |
| • MGH: 110-115%, 120%+ if necessary |
| • Impact of chemotherapy |
| AAPM 2010 |

CALIBRATION OF HYPOXIC REGION FOCUSED RADIOTHERAPY TREATMENT PLANS

CROSS REFERENCE

This application is a continuation-in-part and claims the benefit of U.S. patent application Ser. No. 14/745,188 filed on Jun. 19, 2015, claims the benefit of U.S. patent application Ser. No. 14/436,394 filed on Apr. 16, 2015, which is a 371 of PCT/US13/65283 filed on Oct. 16, 2013, which is a continuation-in-part and claims the benefit of U.S. patent application Ser. No. 13/652,821 filed on Oct. 16, 2012, the specifications of which are incorporated herein in their entirety by reference.

FIELD OF INVENTION

The present invention relates to calibration of radiotherapy methods. More particularly, it relates to calibration of radiotherapy methods for hypoxic region focused tumor treatment.

BACKGROUND OF THE INVENTION

Tumor Hypoxia:

Tumor hypoxia refers to the condition in which cells within a tumor are deprived of oxygen. This condition can occur when a rapidly growing tumor lacks a functional vasculature system and thus has inadequate blood supply to regions in the interior of the tumor. Hypoxic regions within a tumor can be visualized using imaging techniques such as PET. Such non-invasive imaging techniques allow for identification of the boundaries of the hypoxic region or regions.

Phantom Calibration of Radiotherapy Treatment Plans:

Radiotherapy plans are designed to provide sufficient dose levels to target tissues and limit the dose levels to surrounding organs at risk. Given the importance of proper radiation dosing, the treatment plans are routinely calibrated using a phantom before use in a patient. Irradiation of a phantom using the proposed treatment plan allows for a measurement of the actual radiation levels which are delivered using the plan. These actual radiation levels can be compared to the calculated radiation levels and the difference can be used to determine if the treatment plan requires revision.

Radiotherapy Dose Limits:

Radiotherapy is a proven modality for cancer cure like surgery for tumors of all sites. The probability to destroy a cancer locally is proportional to the radiation dose delivered to the cancer site. Most often, an effectiveness of radiotherapy is limited by the radiation does that can safely be delivered to a normal organ adjacent to the tumor. Serious complications may occur if the normal organs received a radiation does that exceeds their tolerance to radiation. Paralysis (spinal cord injury), blindness (optic nerve injury), stroke (brain injury), bleeding (blood vessels injury), inflammation of lung (lungs injury) and bowels (bowels injury) may lead to death or seriously affect patient quality of life. These are well known complications of radiation treatment. Current methods of radiation treatment set a maximum limit for the radiation dose.

For example, in section 6.4.2.4 Radiation Therapy Oncology Group (RTOG) study number 0225: A Phase II Study of Intensity Modulated Radiation Therapy (IMRT) +/ Chemotherapy for Nasopharyngeal Cancer, it is specified that "No more than 20% of any PTV70 (the gross tumor volume with a 5 mm margin) will receive 110% of the prescribed dose." The rule limits the toxicity of treatment to avoid complications.

Figure 1A:
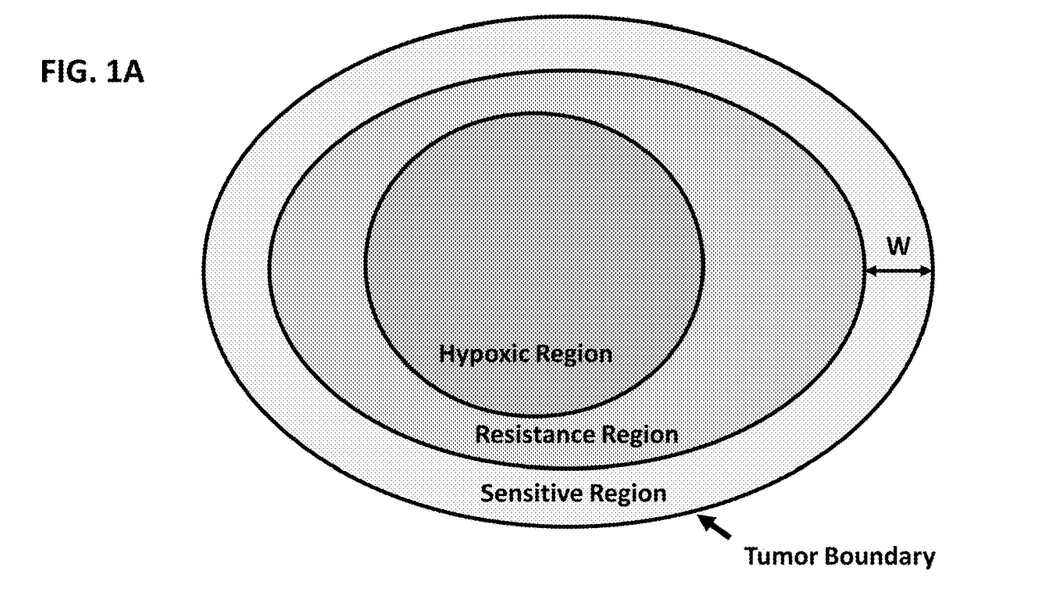
FIG. 1A shows a schematic representation of a tumor with a sensitive region, a resistance region, and a hypoxic region, all within the tumor boundary. The average width of the sensitive region, W, is also shown.
Figure 1B:
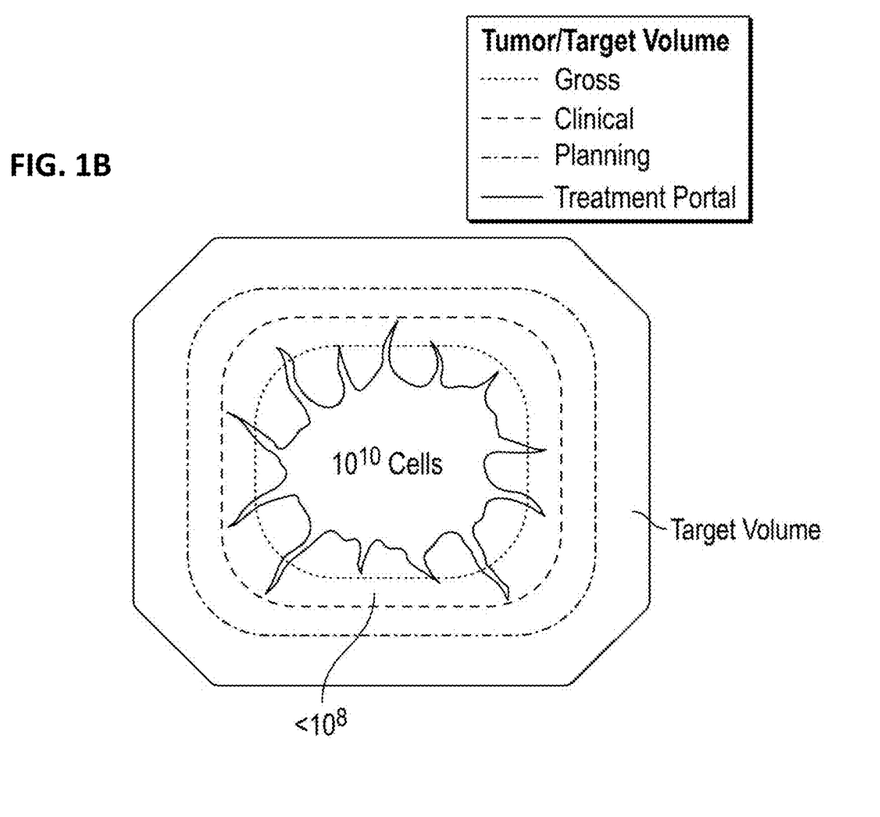
FIG. 1B shows schematic representation of "volumes" in radiation therapy in terms of Gross Target Volume, Clinical Target Volume, Planning Target Volume.

FIG. 1B shows schematic representation of "volumes" in radiation therapy in terms of Gross Target Volume, Clinical Target Volume, Planning Target Volume from Page 5, Chapter 1: The Discipline of Radiation Oncology, Book: Perez and Brady's Principles and Practice of Radiation Oncology, 5th Edition, published by Lippincott Williams & Wilkins with ISBN-10: 078176369X. This figure clearly shows that the planning target volume (PTV) is beyond the tumor boundary.

Table 1 shows the Memorial Sloan-Kettering Cancer Center (MSKCC) Clinical Dose Limits and Inverse Planning Algorithm Constraints for Primary Nasopharynx Tumors, excerpted from book "A practical guide to intensity-modulated radiation therapy" (Medical Physics Pub., 2003, ISBN: 1930524137), Chapter 10: IMRT for head and neck Cancer, Table 10.3, page 201. The table clearly regulates that the maximum dose is 105%.

TABLE 1

| | | Inverse Planning Algorithm Constraint Template | | | |
|---|---|---|---|---|---|
| Structure | Clinical Dose Limits | Prescription Dose (%) | Maximum Dose (%)/Penalty | Minimum Dose (%)/Penalty | Dose (%)-% Volume Constraint/Penalty |
| $PTV_{el}$ | $D_{95} \geq 50$ Gy (95% of 54 Gy) Max. Dose $\leq$ 64.8 Gy (120% of 54 Gy) | 54 Gy (77%) | 56.7 Gy (81%)/50 | 51.3 Gy (73%)/50 | NA |
| $PTV_{gr}$ | $D_{95} \geq 70$ Gy (100% of 70 Gy) Max. Dose $\leq$ 84 Gy (120% of 70 Gy) | 70 Gy (100%) | 66.5 Gy (105%)/50 | 73.5 Gy (95%)/50 | NA |
| Spinal Cord | Max. Dose $\leq$ 45 Gy | | 28 Gy (40%)/50 | | NA |
| Brainstem | Max. Dose $\leq$ 50 Gy | | 35 Gy (50%)/50 | | NA |
| Parotid Gland | Mean Dose $\leq$ 26 Gy | | 68 Gy (98%)/50 | | $\geq$21 Gy (30%) to $\leq$30% Volume/50 |
| Cochlea | Max. Dose $\leq$ 60 Gy | | 56 Gy (80%)/50 | | NA |

Table 2 shows the compliance criteria of radiation treatment in Radiation Therapy Oncology Group (RTOG) study number 0920: A Phase III Study of Postoperative Radiation Therapy (IMRT) +/− Cetuximab for Locally-Advanced Resected Head and Neck Cancer, section 6.7, page 27. The criteria list in Row 1 that any Radiation dose (RT)>66Gy as a major variation should be avoided at any rate. The 66Gy corresponds to a 10% increase over PTV 60Gy.

TABLE 2

|  | Per Protocol | Minor Variation | Major Variation |
| --- | --- | --- | --- |
| Total RT dose to PTV60 (to 95% of PTV60) | 60-64 Gy | 58-60 or 64-66 Gy | <58 or >66 Gy |
| Minimum dose ("cold spot") within PTV60, not including portion of PTV near (<8 mm) skin) | 56-60 Gy | 54-56 Gy | <54 Gy |
| Maximum dose ("hot spot") within PTV60* | <70 Gy | 70-72 Gy | >72 Gy |
| Maximum dose ("hot spot") outside of PTV60) | <66 Gy | 66-70 Gy | >70 Gy |
| Definition of CTV60 | Base on case review by study chair. | | |
| Definition of PTV60 | Base on case review by study chair. | | |
| Total RT dose to spinal cord PRV (0.03 cm$^3$) | <48 Gy | 48-50 Gy | >50 Gy |
| Total RT dose to spinal cord PRV (0.01 cm$^3$) | <50 Gy | 50-52 Gy | >52 Gy |
| Definition of Spinal cord PRV | Base on case review by study chair. | | |
| Overall RT treatment time |  |  | >50 days (without a medically appropriate indication for delay) |
| Non-Medically Indicated Treatment Interruptions | 0-2 | 2-4 | >4 |

*Not including the region of PTV60 that falls within PTV66 (if applicable)

Table 3 shows the Critical Normal Structures in Radiation Therapy Oncology Group (RTOG) study number 0225: A Phase II Study of Intensity Modulated Radiation Therapy (IMRT) +/ Chemotherapy for Nasopharyngeal Cancer, section 6.4.3 Critical Normal Structures, page 7. The Critical Normal Structures discloses clearly that 60 Gy or 1% of the PTV cannot exceed 65 Gy (which is close to 10% increase over PTV 60Gy radiation.

TABLE 3

Critical Normal Structures 6.4.3 DVH's must be generated for all critical normal structures and the unspecified tissues.
Dose
constraints to normal tissues will be as follows:
Brainstem, optic nerves, chiasm   54 Gy or 1% of the PTV cannot exceed 60 Gy
Spinal Cord                       45 Gy or 1 cm$^3$ (if 1% is used, depends on length of
                                  the cord outlined) of the PTV cannot exceed 50 Gy
Mandible and T-M joint            70 Gy or 1 cm$^3$ of the PTV cannot exceed 75 Gy
Temporal lobes                    60 Gy or 1% of the PTV cannot exceed 65 Gy
Unspecified tissue outside the targets: ≤100% of the dose prescribed to PTV$_{70}$. No more
than 5% of the non-target tissue can receive greater than 70 Gy. Participants are strongly
encouraged to remain within these limits.

Figure 2:
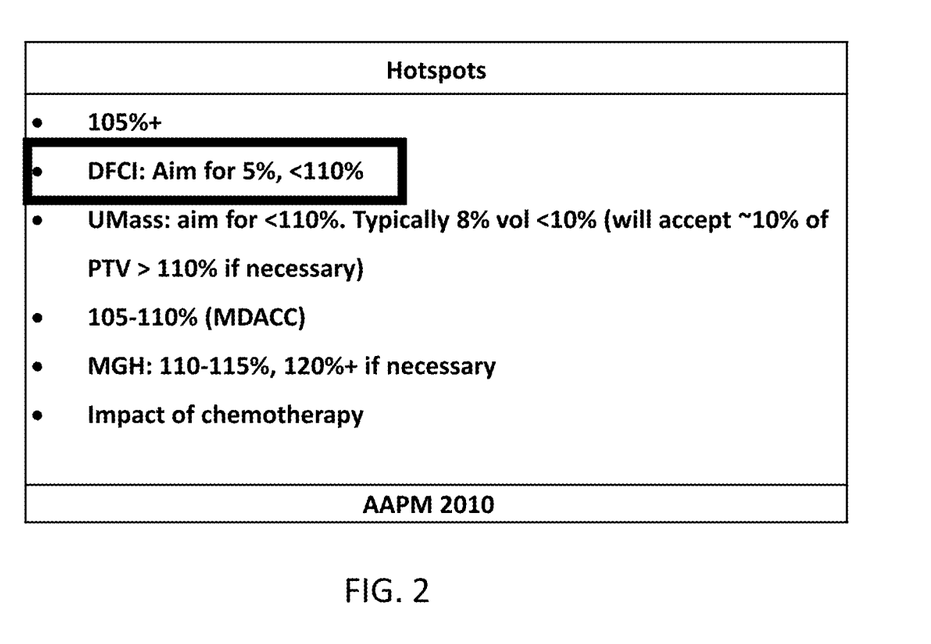
FIG. 2 shows the hotspot radiation regulation in a presentation (slide 13) of a research taken at Dana-Farber/Brigham & Women's Cancer Center and Harvard Medical School.
Figure 3:
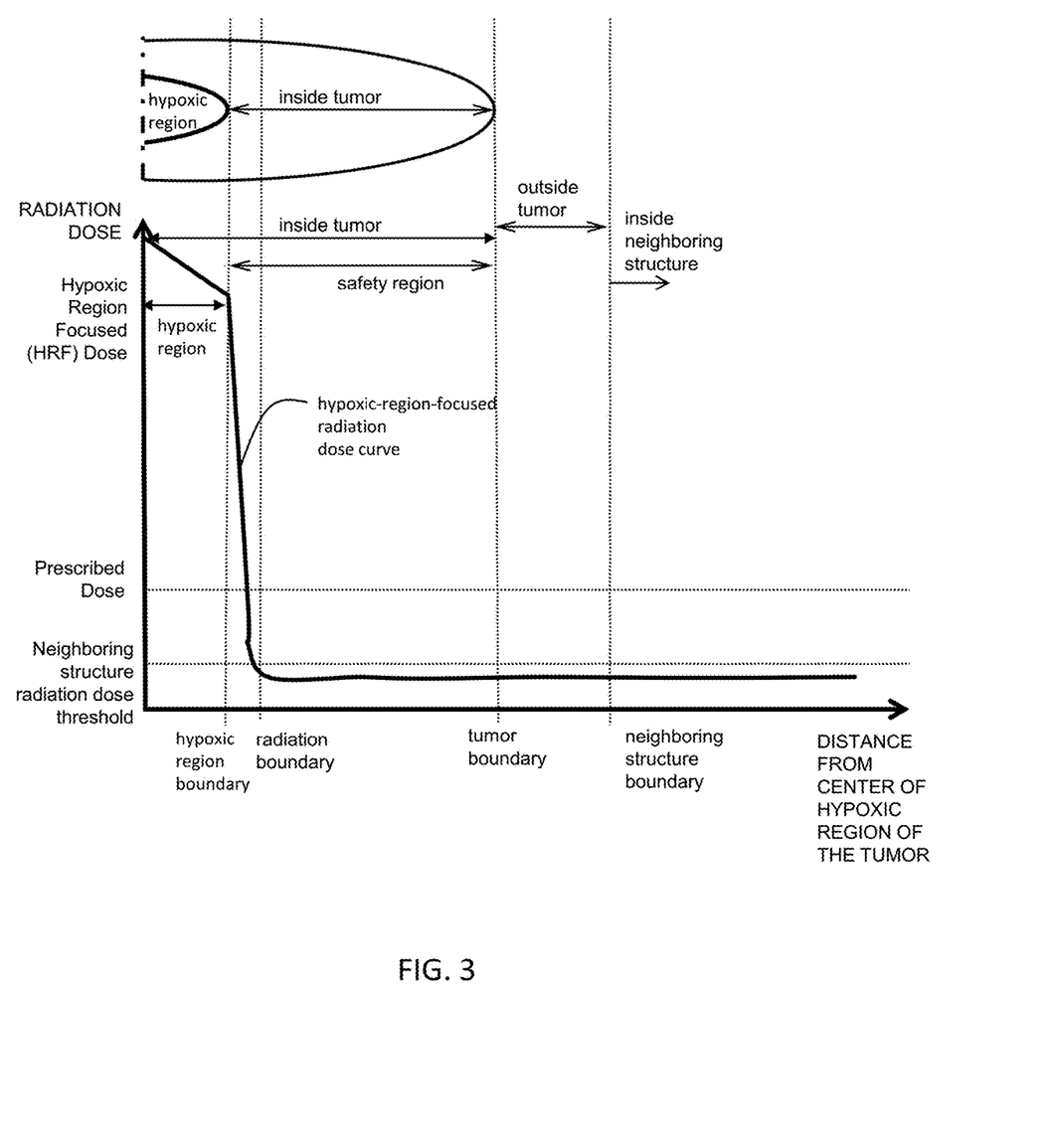
FIG. 3 is a schematic drawing of a tumor and the hypoxic region of the tumor. High HRF radiation dosage is applied in the hypoxic region. The figure is not to scale.
Figure 4:
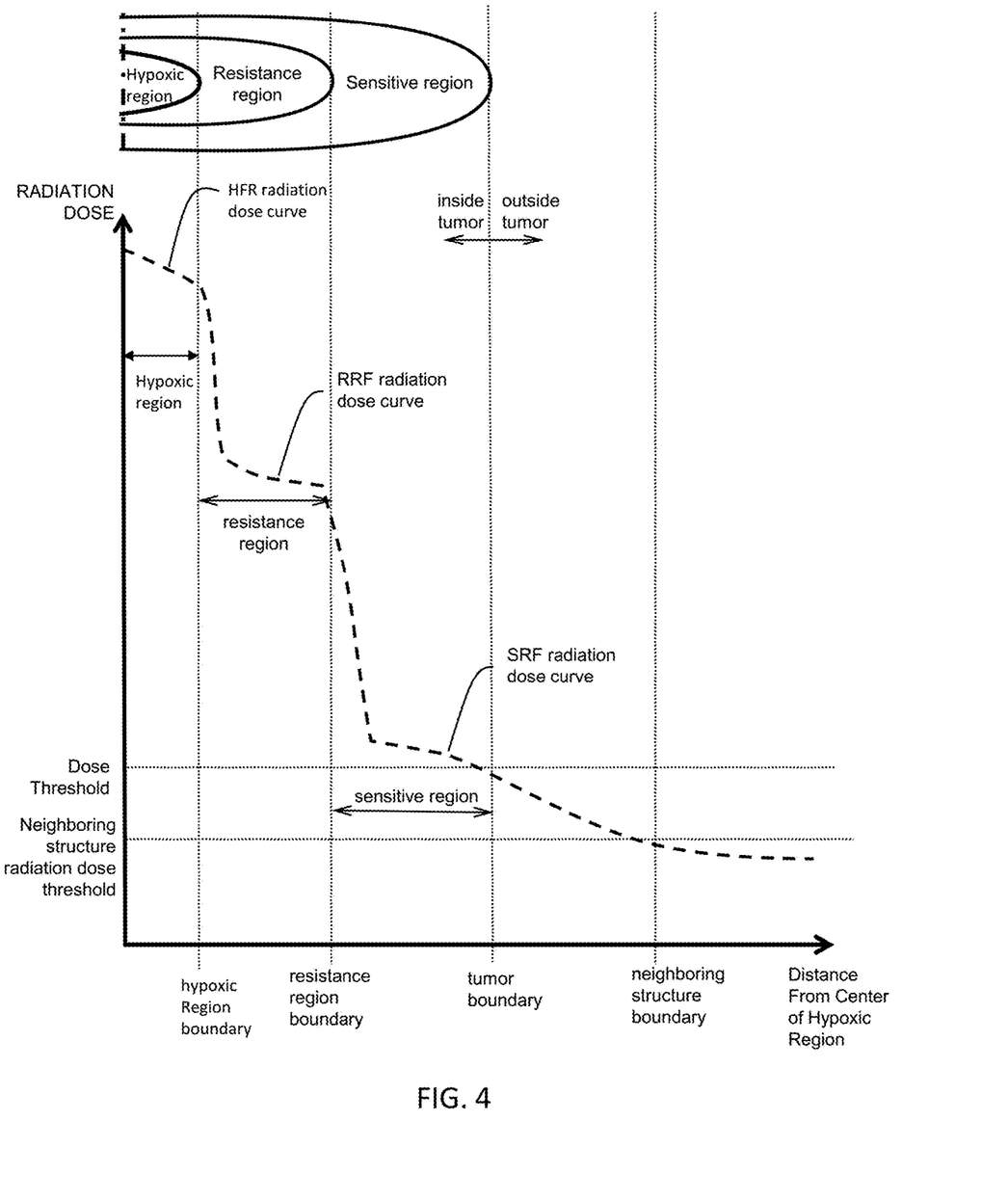
FIG. 4 is a schematic drawing of a tumor with a hypoxic region, a resistance region, and a sensitive region. A HRF radiation dose is applied in the hypoxic region, a RRF radiation dose is applied in the resistance region, and a SRF radiation dose is applied in the sensitive region of the tumor. At the tumor boundary, the dose is lower than a dose threshold. At the neighboring structure boundary, the dose is lower than a neighboring structure dose threshold. The figure is not to scale.
Figure 5A:
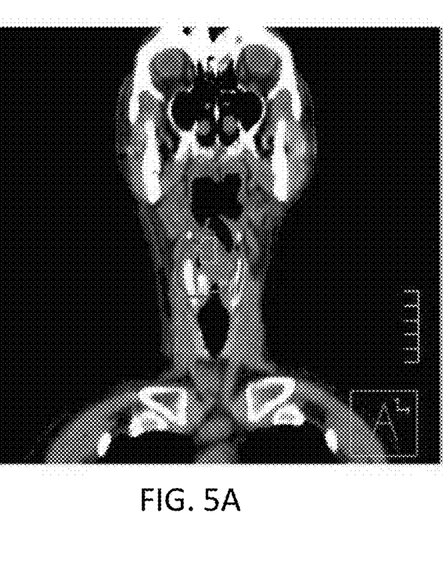
FIG. 5A and FIG. 5B are front views of clinical results showing tumor mass being removed due to high dosage radiation therapy by image guided boosted region technology.
Figure 5B:
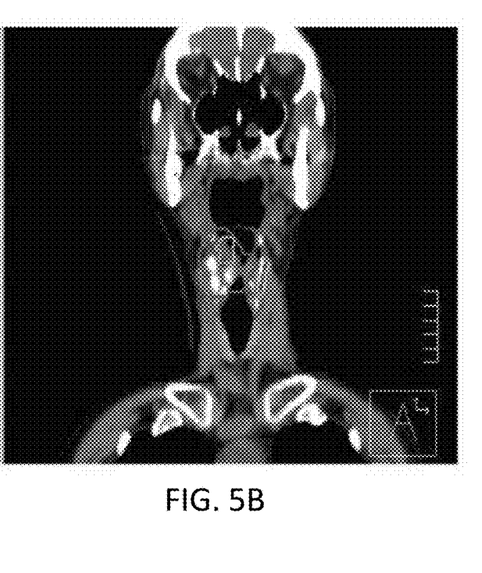
Figure 6A:
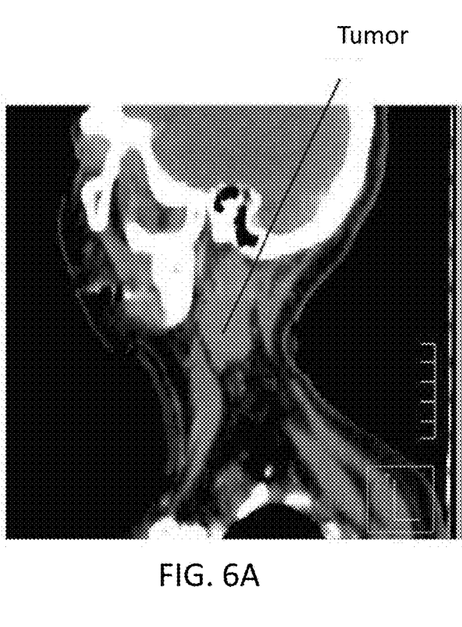
FIG. 6A and FIG. 6B are side views of clinical results showing tumor mass being removed due to high dosage radiation therapy by image guided boosted region technology.
Figure 6B:
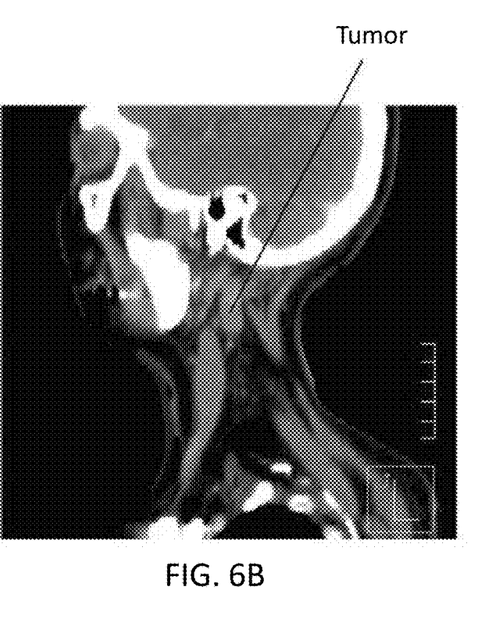

FIG. 2 shows the hotspot radiation regulation in a presentation (slide 13) of a research taken at Dana-Farber/Brigham & Women's Cancer Center and Harvard Medical School ("Variability in planning criteria and plan evaluation", Laurence Court, the American Association of Physicists in Medicine annual meeting 2010). The slide clearly shows the aiming for hotspots radiation is limited to <110% of the radiation dose.

However, a use of low radiation dose can be ineffective for curing cancer and a patient can die from uncontrolled tumor growth or from complications resulting from tumor destruction of normal organs. Thus, a clinician is often faced with a dilemma: either let the cancer kill the patient or expose the patient to serious injury from radiation complications. Therefore, there is a need for a balanced method for image-guided radiotherapy for providing higher dose for tumor tissue, such as hypoxia region of tumor, while avoiding excessive radiation to normal tissue.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features calibration of an image-guided radiotherapy treatment plan for a hypoxic tumor. The treatment plans feature a hypoxic region focused (HRF) dose which may be greater than 120% of a predetermined prescribed radiation dose for the tumor. Additionally, the treatment plans may feature a resistance region focused (RRF) dose which is greater than the predetermined prescribed dose and less than the HRF dose.

One of the unique and inventive technical features of the present invention is that three-dimensional imaging is used to identify a hypoxic region of a tumor, and a resistance region is designated between the hypoxic region and a sensitive region. Without wishing to limit the invention to any theory or mechanism, it is believed that the technical feature of the present invention advantageously provides for calibration of HRF and RRF doses using irradiation of a phantom. None of the presently known prior references or work has the unique inventive technical feature of the present invention.

BRIEF DESCRIPTION OF THE DRAWINGS

The features and advantages of the present invention will become apparent from a consideration of following detailed description presented in connection with the accompanying drawings in which.

DETAILED DESCRIPTION OF THE INVENTION

As used herein, "hypoxic region" refers to a tumor region which has inadequate oxygen. As a non-limiting example, a hypoxic region may be a region in which is identified using a PET scan and a hypoxia sensitive biomarker. As used herein, "resistance region" refers to a tumor region which exhibits radiation resistant properties. As a non-limiting example, a resistance region may be a region in which surrounds the hypoxic area and in which the cancer cells are primarily dormant and non-dividing.

As used herein, the terms "prescribed radiation dose" or "prescribed dose" means the conventional dose established in the literature for cancer cure. The prescribed dose may be determined from external beam radiotherapy alone or radiotherapy combined with chemotherapy for locally advanced head and neck cancer. As non-limiting examples, the "prescribed dose" for Oropharyngeal cancer, Oral cavity cancer, Laryngeal cancer, Hypopharyngeal cancer is about 7000 cGy, at about 200 cGy per day.

As used herein "homogenous" refers to the quality of being substantially the same or similar throughout. For example, a homogenous dose may refer to a dose which is substantially the same throughout the homogenous volume. As another example a homogenous dose may refer to a dose which has no point throughout the homogenous volume where the dose differs from an average dose for the homogenous volume by more than about 1, 2, 3, 5, 10, or 15 percent. As used herein, the terms "boosted radiation dose" or "boosted dose" is defined as a dose that is at least 110% higher than the prescribed dose.

In one embodiment, the present invention features a method of calibrating a resistance region focused (RRF) dose in a radiotherapy treatment plan for a tumor using a phantom model. As a non-limiting example, the method may comprise: obtaining a three-dimensional image of a tumor in a patient; identifying a peripheral boundary of the tumor using the three-dimensional image; identifying a hypoxic region within the tumor using the three-dimensional image; designating a region immediately inside the peripheral boundary as a sensitive region, the sensitive region having an average width W; designating a region between the hypoxic region and the sensitive region as a resistance region; generating a radiation treatment plan; irradiating a phantom following the treatment plan; measuring the irradiation in said phantom; testing the measured irradiation to the phantom region corresponding to the peripheral boundary to determine if the boosted RRF dose had increased irradiation at the peripheral boundary above a threshold value; and calibrating the RRF dose based on the determination of the irradiation to the phantom region corresponding to the peripheral boundary.

In a preferred embodiment, the treatment plan may comprise: a hypoxic region focused (HRF) dose, the HRF dose directed to the hypoxic region; a resistance region focused (RRF) dose, lower than the HRF dose but boosted above a spillover dose from the HRF dose, the RRF dose directed to the resistance region; and a sensitive region focused (SRF) dose, lower than the RRF dose, the SRF dose directed to the sensitive region.

In some embodiments, the tumor may be a radiation resistant tumor. In other embodiments, the three-dimensional image may be obtained using positron-emission tomography (PET). In still other embodiments, the HRF radiation dose or the RRF radiation dose may be greater than a prescribed treatment dose for the tumor. In yet other embodiments, a combined volume of the resistance region and the hypoxic region may be more than 20% of a total volume of the tumor. As a non-limiting example, the combined volume of the resistance region and the hypoxic region may be more than 25, 30, 35, 40, 45, 50, 60, 70, 80, 90, 95, or 99 percent of a total volume of the tumor.

In a selected embodiment, the present invention may feature an image-guided radiotherapy method for treatment of a tumor. As a non-limiting example, the method may comprise: obtaining a three-dimensional image of a tumor in a patient; identifying a peripheral boundary of the tumor; identifying a hypoxic region within the tumor using the three-dimensional image; designating a region immediately inside the peripheral boundary as a sensitive region, the sensitive region having an average width W; designating a region between the hypoxic region and the sensitive region as a resistance region; designating and applying a hypoxic region focused (HRF) radiation dose to the hypoxic region; and designating and applying a resistance region focused (RRF) radiation dose to the resistance region. According to one embodiment, the HRF radiation dose may be greater than the RRF radiation dose.

In some embodiments, the method may further comprise designating and applying a sensitive region focused (SRF) radiation dose to the sensitive region. As a non-limiting example, the SRF radiation dose may be lower than the RRF radiation dose. In some additional embodiments, the radiation doses may be escalated in an iterative manner. As a non-limiting example, a patient may be treated with a first radiation dose, imaged to determine the effect of the radiation dose on the tumor, and treated with a second radiation dose which is either larger or smaller than the first radiation dose, depending on if the effect of the radiation dose on the tumor.

In one embodiment, the HRF radiation dose or the RRF radiation dose may be greater than a prescribed treatment dose for the tumor. In another embodiment, the RRF dose may be greater than a spillover dose from the HRF dose. As a non-limiting example, a spillover dose may decrease 10% in intensity with each additional mm of distance from the region to which the dose was directed. As another non-limiting example, a spillover dose may decrease 1, 2, 3, 4, 5, 7, 15, 20, 30, 40, 50, 60, 70, 80, or 90% in intensity with each additional mm of distance from the region to which the dose was directed. According to one preferred embodiment, the tumor may be larger than about 3 cm in diameter. According to another preferred embodiment, the tumor may be larger than about 0.5, 1, 1.5, 2, 2.5, 3.5, 4, 4.5, 5, 6, 7, 8, 9, or 10 cm in diameter.

In another embodiment, the present invention features an image-guided radiotherapy method for treatment of a tumor. As a non-limiting example, the method may comprise: obtaining a three-dimensional image of a tumor; identifying a hypoxic region of the tumor, using the three-dimensional image; and designating and applying a hypoxic region focused (HRF) radiation dose to the hypoxic region. In a preferred embodiment, the HRF radiation dose may be at least 120 percent of a prescribed treatment dose for the tumor. In other preferred embodiments, the HRF radiation dose may be at least 105, 110, 115, 125, 130, 140, 150, 160, 170, 180, 190, 200, 250, 300, 400, 500 or 1000 percent of a prescribed treatment dose for the tumor. In some embodiments, the HRF radiation dose may be at least 30 Gy. In other embodiments, the HRF radiation dose may be at least 5, 10, 15, 20, 25, 35, 40, 45, 50, 60, 70, 80, 90, or 100 Gy.

In some embodiments, the dose may reflect the dose delivered in one treatment session. In other embodiments, the dose may reflect the total dose delivered over a number of treatment sessions. According to yet other embodiments, the method may further comprise designating a resistance region within the tumor and applying a resistance region focused (RRF) radiation dose to the resistance region. As a non-limiting example, the RRF radiation dose may be lower than the HRF radiation dose.

In some embodiments, the three-dimensional image may be obtained using positron-emission tomography (PET). In other embodiments, the three-dimensional image may be obtained by magnetic resonance spectroscopy (MRS) or MRI. In a selected embodiment, the HRF radiation dose or the RRF radiation dose may greater than a prescribed treatment dose for the tumor. As a non-limiting example, the HRF radiation dose may be at least about 5, 10, 15, 20, 25, 30, 35, 40, 45, 50, 55, 60, 65, 70, 80, 90, or 100 Gy. As another non-limiting example, the RRF radiation dose may be at least about 5, 10, 15, 20, 25, 30, 35, 40, 45, 50, 55, 60, 65, 70, 80, 90, or 100 Gy. In some embodiments the HRF may be about 105, 110, 115, 120, 130, 140, 150, 160, 170, 180, 190, 200, 250, 300, 350, 400, 450, 500, 600, 700, 800, 900, or 1000 percent of the RRF dose. According to another embodiment, the method may further comprise designating and applying a sensitive region focused (SRF) radiation dose to the sensitive region. In preferred embodiments, the SRF radiation dose may be lower than the RRF radiation dose. In some embodiments the RRF may be about 105, 110, 115, 120, 130, 140, 150, 160, 170, 180, 190, 200, 250, 300, 350, 400, 450, 500, 600, 700, 800, 900, or 1000 percent of the HRF dose.

In one embodiment, a volume of the hypoxic region may be more than 20% of a total volume of the tumor. In other embodiments, the volume of the hypoxic region may be more than 1, 2, 5, 10, 15, 25, 30, 40, 50, 60, 70, 80, 90 or 95% of a total volume of the tumor. In another embodiment, a combined volume of the resistance region and the hypoxic region may be more than 20% of a total volume of the tumor. In still other embodiments, the combined volume of the resistance region and the hypoxic region may be more than 1, 2, 5, 10, 15, 25, 30, 40, 50, 60, 70, 80, 90 or 95% of a total volume of the tumor. In an embodiment, the average width of the sensitive region, W, may be about 0.1, 0.5, 1, 2, 3, 4, 5, 6, 7, 8, 9, 10, 11, 12, 13, 14, 15, 16, 17, 18, 19, or 20 mm. In some embodiments the width of the sensitive region may be constant. In other embodiments, the width of the sensitive region may vary. According to one non-limiting example, a tumor having an average diameter of about 3 cm may have a sensitive region width of about 3-4 mm. According to another non-limiting example, a tumor having an average diameter of about 5 cm may have a sensitive region width of about 3-5 mm. According to yet another non-limiting example, a tumor having an average diameter of about 10 cm may have a sensitive region width of about 10 mm.

In another embodiment, the radiation doses may be escalated in an iterative manner. As a non-limiting example, an iterative treatment plan may double or triple the dose from one treatment to the next or reduce the dose from one treatment to the next. In yet another embodiment, the HRF dose may be homogenous over 95 percent by volume of the hypoxic region. In alternative embodiments, the HRF dose may be homogenous over 5, 10, 15, 20, 25, 30, 40, 50, 60, 70, 80, 90 or 99 percent by volume of the hypoxic region. Similarly, in some embodiments, the RRF dose may be homogenous over 95 percent by volume of the resistance region. In other alternative embodiments, the RRF dose may be homogenous over 5, 10, 15, 20, 25, 30, 40, 50, 60, 70, 80, 90 or 99 percent by volume of the resistance region.

The HRF radiation dose may be over 120% of a predetermined prescribed radiation dose for the tumor (110). As a non-limiting example, for radiation sensitive tumors, the predetermined prescribed radiation dose may range from about 180-200 centiGray per day and the HRF radiation dose may range from about 360 to 400 centiGray per day. As another non-limiting example, for radiation resistant tumors, the predetermined prescribed radiation dose may be about 250 centiGray per day and the HRF radiation dose may be about 500 centiGray per day.

Due to tail effect of an HRF radiation beam, a safety distance may affect the maximum HRF radiation dose. The HRF radiation dose may decrease at a rapid rate with increasing distance from the center of the hypoxic region such that sensitive region of the tumor (110) receives less than 40% of the HRF radiation dose.

According to some embodiments, the tumor may be a radiation resistant tumor. Examples of tumors that can be treated using this method include radiation sensitive tumors and radiation resistant tumors. Non-limiting examples of radiation sensitive tumors include: Squamous Carcinoma, Adeno Carcinoma, Small Cell Carcinoma, Lymphoma Carcinoma and Transitional Cell Carcinoma. Non-limiting examples of radiation resistant tumors include Melanoma and Renal cancer.

EXAMPLES

Example 1

The image-guided radiotherapy treatment plans in Table 4 may be calibrated using a phantom:

TABLE 4

Example image-guided radiotherapy treatment plans

|  | Example 1 | Example 2 | Example 3 | Example 4 | Example 5 | Example 6 |
|---|---|---|---|---|---|---|
| Sensitive region dose | 0 Gy | 2 Gy | 2 Gy | 2 Gy | 2 Gy | 2 Gy |
| Resistance region dose | 5 Gy | 5 Gy | 10 Gy | 15 Gy | 20 Gy | 40 Gy |
| Hypoxic region dose | 10 Gy | 10 Gy | 20 Gy | 30 Gy | 40 Gy | 80 Gy |

Example 2

A patient may be treated according to any of the image-guided radiotherapy treatment plans in Table 4.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of calibrating a resistance region focused (RRF) dose in a radiotherapy treatment plan for a tumor using a phantom model, the method comprising:
    a. obtaining a three-dimensional image of a tumor in a patient;
    b. identifying a peripheral boundary of the tumor using the three-dimensional image;
    c. identifying a hypoxic region within the tumor using the three-dimensional image;
    d. designating a region immediately inside the peripheral boundary as a sensitive region, the sensitive region having an average width W;
    e. designating a region between the hypoxic region and the sensitive region as a resistance region;
    f. generating a radiation treatment plan, the treatment plan comprising:
        i. a hypoxic region focused (HRF) dose, the HRF dose directed to the hypoxic region;
        ii. a resistance region focused (RRF) dose, lower than the HRF dose but boosted above a spillover dose from the HRF dose, the RRF dose directed to the resistance region; and
        iii. a sensitive region focused (SRF) dose, lower than the RRF dose, the SRF dose directed to the sensitive region;
        iv. a tumor boundary dose, lower than a threshold dose;
    g. irradiating a phantom following the treatment plan;
    h. measuring the irradiation in said phantom;
    i. testing the measured irradiation to the phantom region corresponding to the peripheral boundary to determine if the boosted RRF dose had increased irradiation at the peripheral boundary above the threshold value; and
    j. calibrating the RRF dose based on the determination of the irradiation to the phantom region corresponding to the peripheral boundary.

2. The method of claim 1, wherein the tumor is a radiation resistant tumor.

3. The method of claim 1, wherein the three-dimensional image is obtained using positron-emission tomography (PET).

4. The method of claim 1, wherein the HRF radiation dose is greater than a prescribed treatment dose for the tumor.

5. The method of claim 1, wherein the RRF radiation dose is greater than a prescribed treatment dose for the tumor.

6. The method of claim 1, wherein a combined volume of the resistance region and the hypoxic region is more than 20% of a total volume of the tumor.

* * * * *